Figure 5:
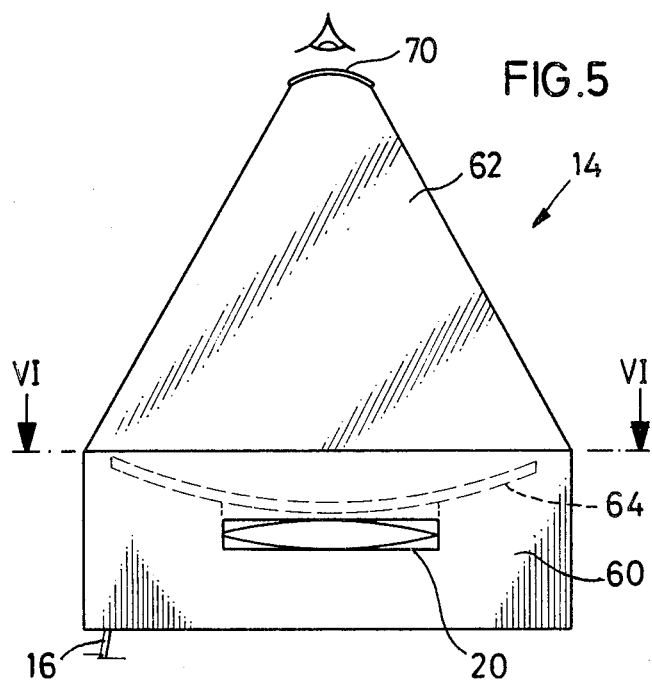

United States Patent [19]
Woolf

[11] 3,982,828
[45] Sept. 28, 1976

[54] EYE TESTING APPARATUS
[75] Inventor: Bernard Nathan Woolf, Muizenberg, South Africa
[73] Assignee: South African Inventions Development Corporation, Pretoria, South Africa
[22] Filed: Aug. 7, 1975
[21] Appl. No.: 602,675

[30] Foreign Application Priority Data
Aug. 8, 1974 South Africa.................. 74/5063

[52] U.S. Cl. ................................ 351/23; 351/17
[51] Int. Cl.² ............................................ A61B 3/02
[58] Field of Search ............................ 351/23, 17

[56] References Cited
UNITED STATES PATENTS

| | | | |
|---|---|---|---|
| 3,025,755 | 3/1962 | Koetting .............................. | 351/23 |
| 3,172,404 | 3/1965 | Copenharer et al. ................. | 351/17 |
| 3,883,234 | 5/1975 | Lynn ................................... | 351/23 |

Primary Examiner—Harold A. Dixon
Attorney, Agent, or Firm—Larson, Taylor & Hinds

[57] ABSTRACT

Eye testing apparatus including a control unit having a control display panel having a number of distributed electrical lights adapted to be illuminated; and electrical connection means for connecting the control unit to a source of electrical energy; a remote scanner unit adapted to be electrically connected to the control unit, and including a scanner display panel provided with electrical lights, positioned corresponding to the lights on the control display panel, and which are adapted to be illuminated corresponding to the illumination of the lights on the control display panel, the scanner display panel also having a fixing light; and operation means for causing any one or more lights on the control display panel and the corresponding light or lights on the scanner display panel to be illuminated for observation by a person viewing the scanner display panel.

12 Claims, 9 Drawing Figures

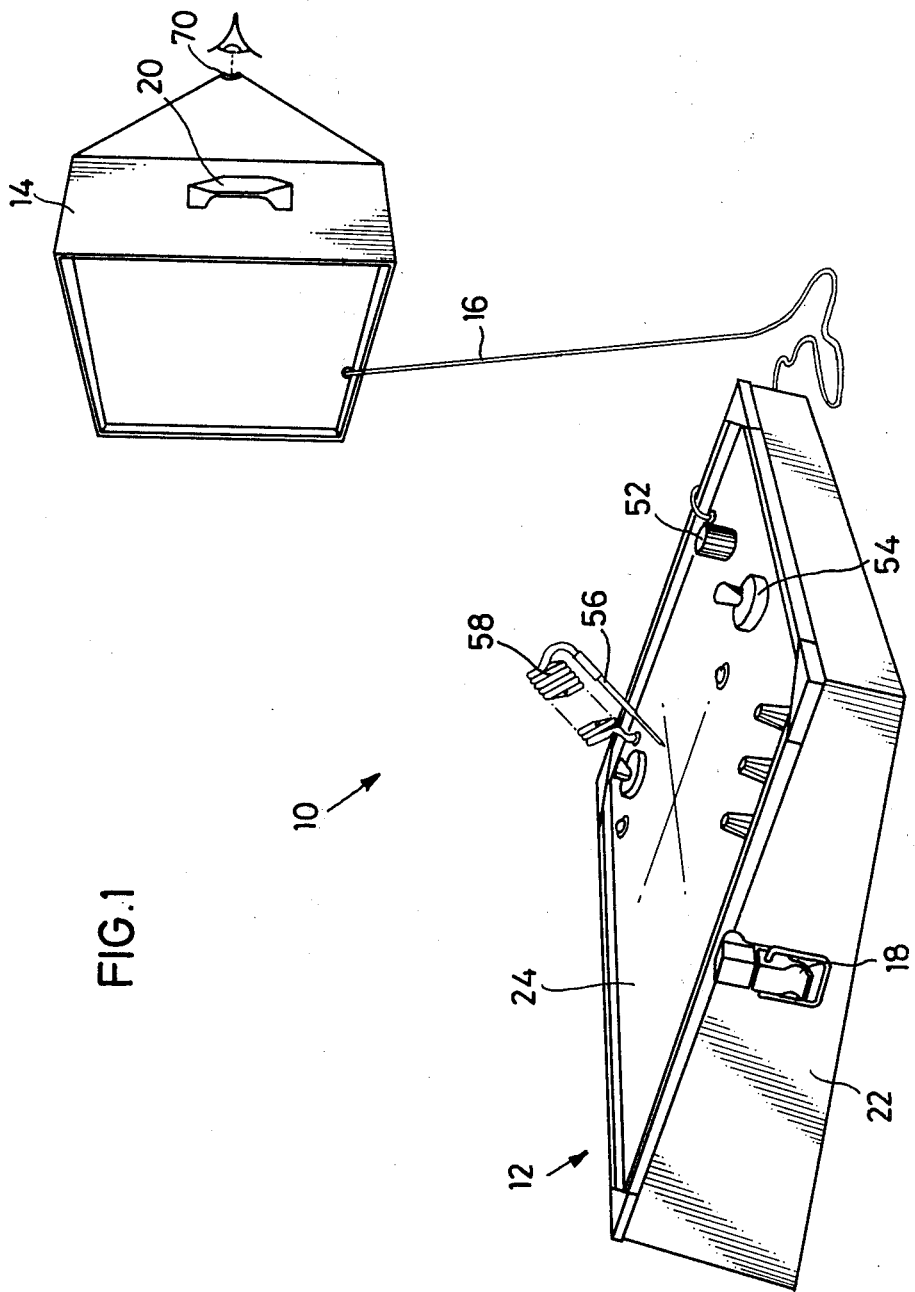

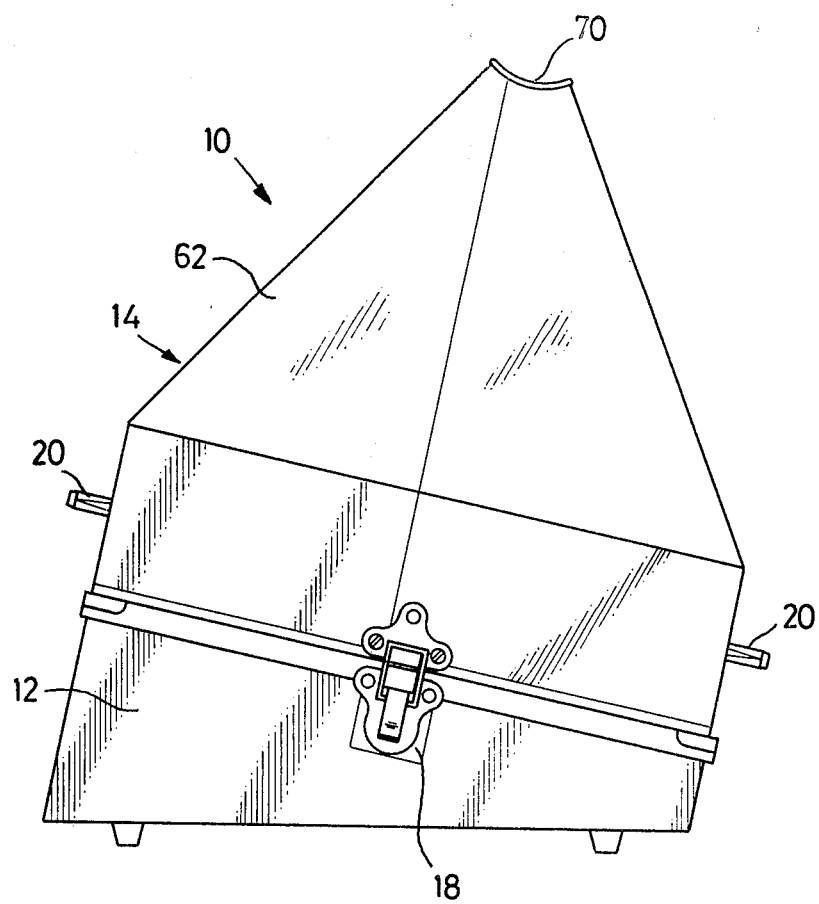

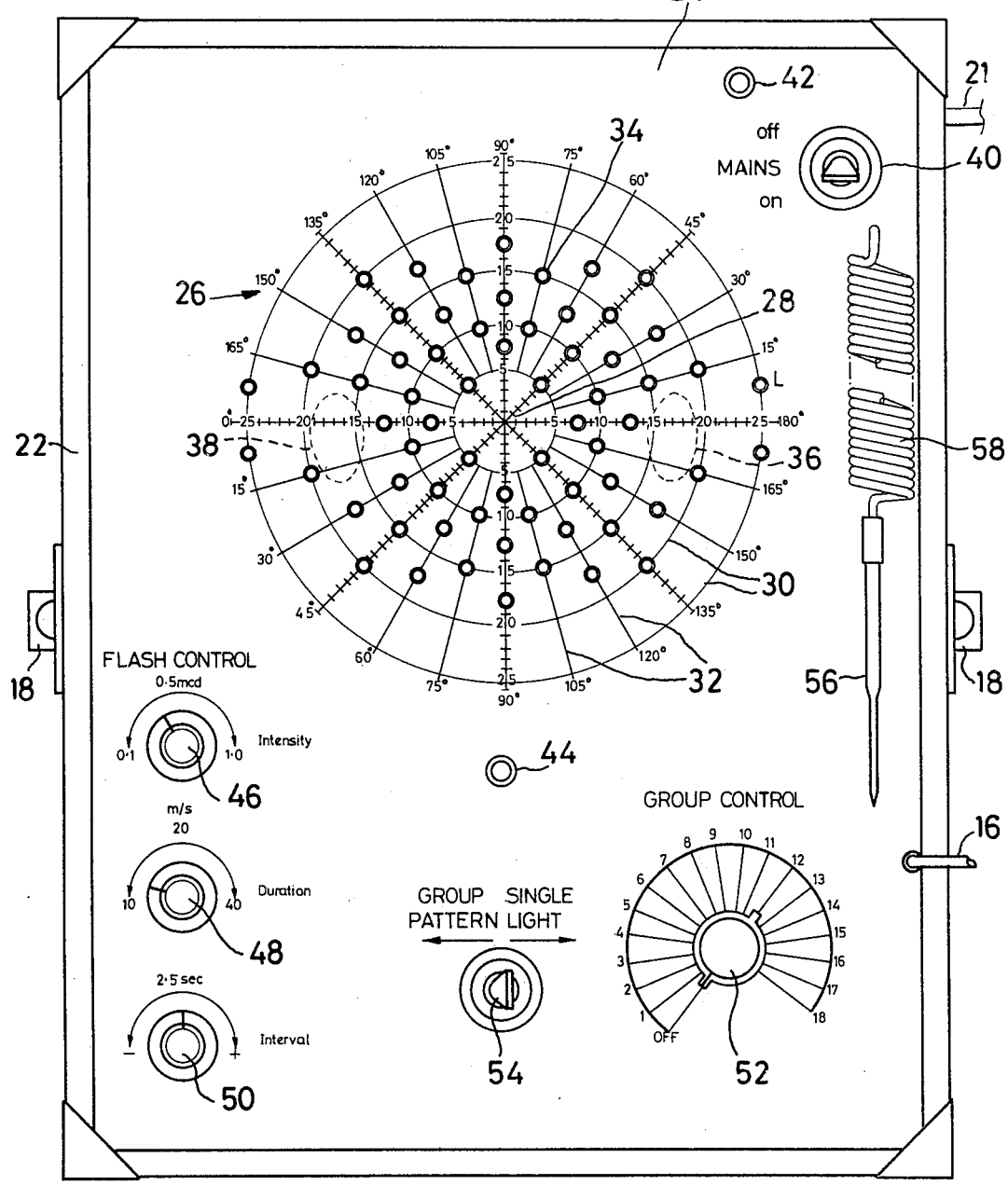
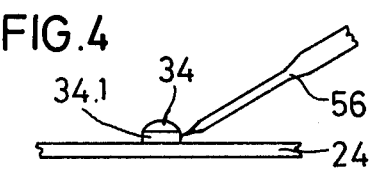

3,982,828

EYE TESTING APPARATUS

The present invention relates to an eye testing apparatus.

More particularly, the invention relates to an eye testing apparatus for determining the existence of the eye disease, known as 'scotoma'.

The eye disease scotoma indicates a blind or partially blind area in the visual field, caused as a result of disease of the retina or any optic nerve. It also is used to describe the appearance of a black spot in the eyes, as in choroiditis.

There are some prior devices for detecting the existence of scotoma. There is for instance the Harrington-Vlok apparatus in which groups of dots on a chart are illuminated by means of ultra-violet light in a darkened room, the Friedman Field Analyser using rotating discs to vary positions of light dots and the Fincham Sutcliffe Scotoma Detector using a chart provided with light bulbs. All of these devices require a darkened testing room.

It is an object of the invention to provide an eye testing apparatus which does not require a darkened room for testing purposes.

According to the invention, an eye testing apparatus includes a control unit having a control display panel having a number of distributed electrical lights adapted to be illuminated; an electrical connection means for connecting the control unit to a source of electrical energy; a remote scanner unit adapted to be electrically connected to the control unit, and including a scanner display panel provided with electrical lights, positioned corresponding to the lights on the control display panel, and which are adapted to be illuminated corresponding to the illumination of the lights on the control display panel, the scanner display panel also having a fixing light; and operation means for causing any one or more lights on the control display panel and the corresponding light or lights on the scanner display panel to be illuminated for observation by a person viewing the scanner display panel.

Each light may be provided with an electrical contact by means of which such light can be caused to be illuminated. The electrical contact may be in the form of an electrically conducting sheath surrounding the light.

The operation means may include an electrically conducting marking device, connected by means of a cable to the control unit, and on contact with the electrical contact of a light causing such light to be illuminated.

The apparatus may include flashing means for illuminating the lights in flashing manner.

The scanner unit may include a housing fully enclosing the scanner display panel, the housing having a viewing opening adapted to be placed for observation against the eye of a person. The scanner unit may include a box shaped housing including the scanner display panel and a funnel shaped hood having a converging part, and a viewing opening being provided in the converging part of the funnel shaped hood.

The apparatus may include light intensity adjusting means for varying for light intensity of the lights, and it may further include duration adjustment means for varying the period and duration of flash of the lights.

Group control means may be provided for allowing a group of lights to be illuminated simultaneously.

The control display panel of the control unit may have locating means for locating a test sheet to be placed on the control display panel, and the locating means may be provided in that the lights on the control display panel stand proud of the display panel for allowing location of a test sheet provided with openings corresponding to the lights.

The invention will now be described by way of example with reference to the accompanying schematic drawings.

In the drawings there is shown in

Figure 6:
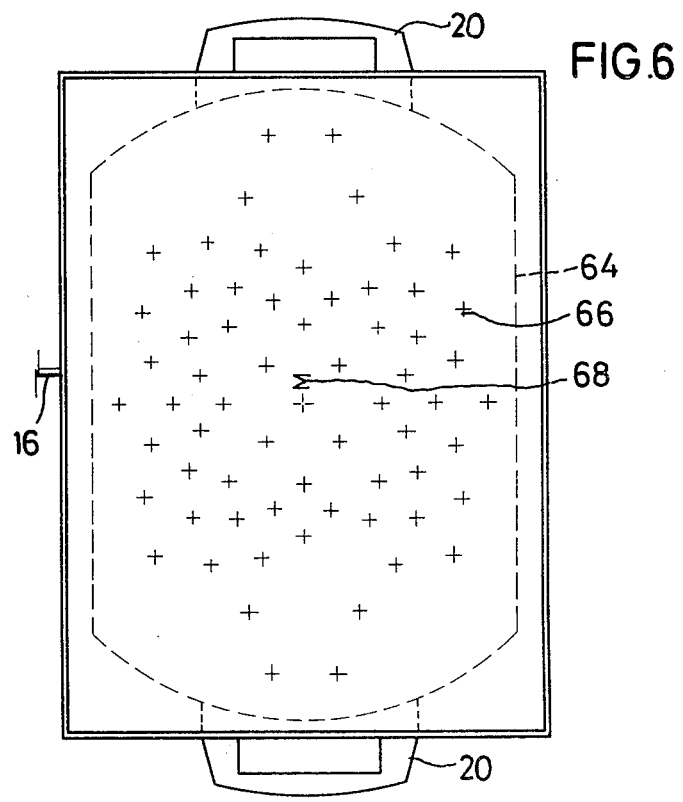
Figure 7:
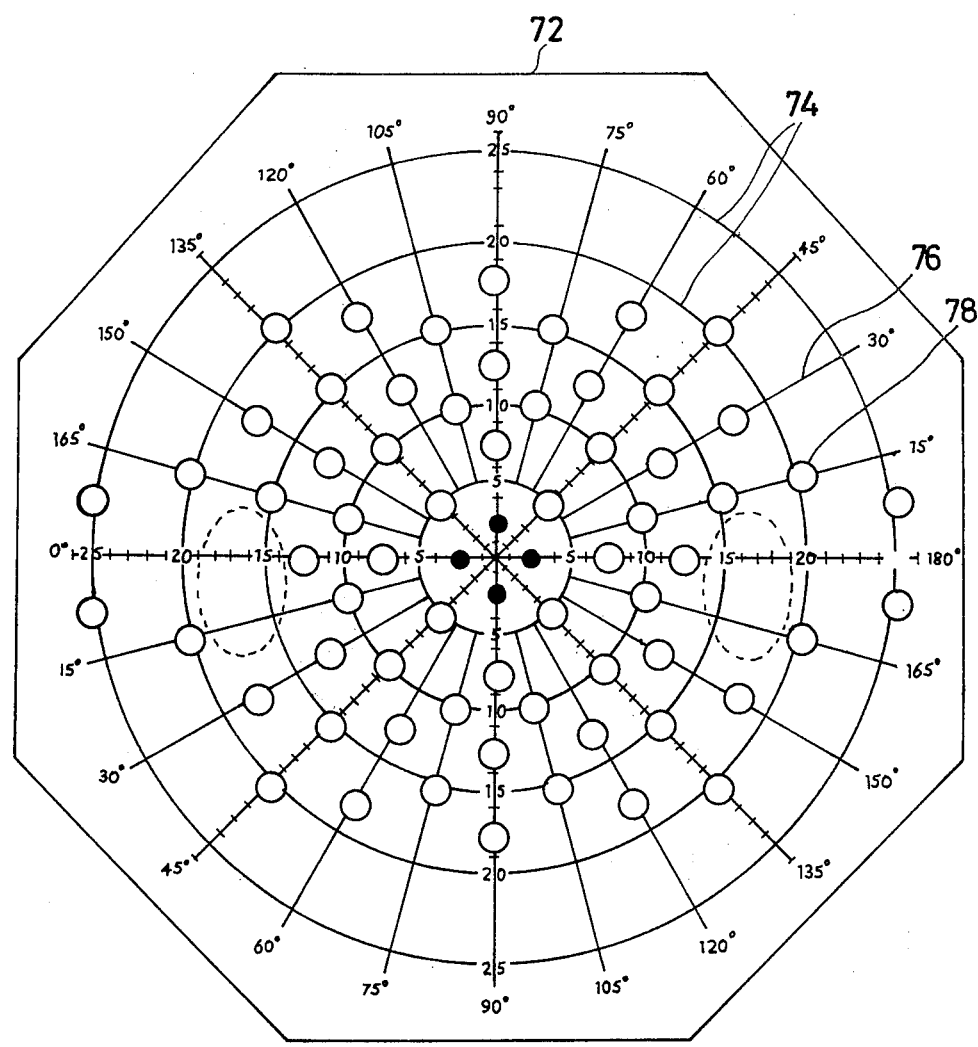
Figure 8:
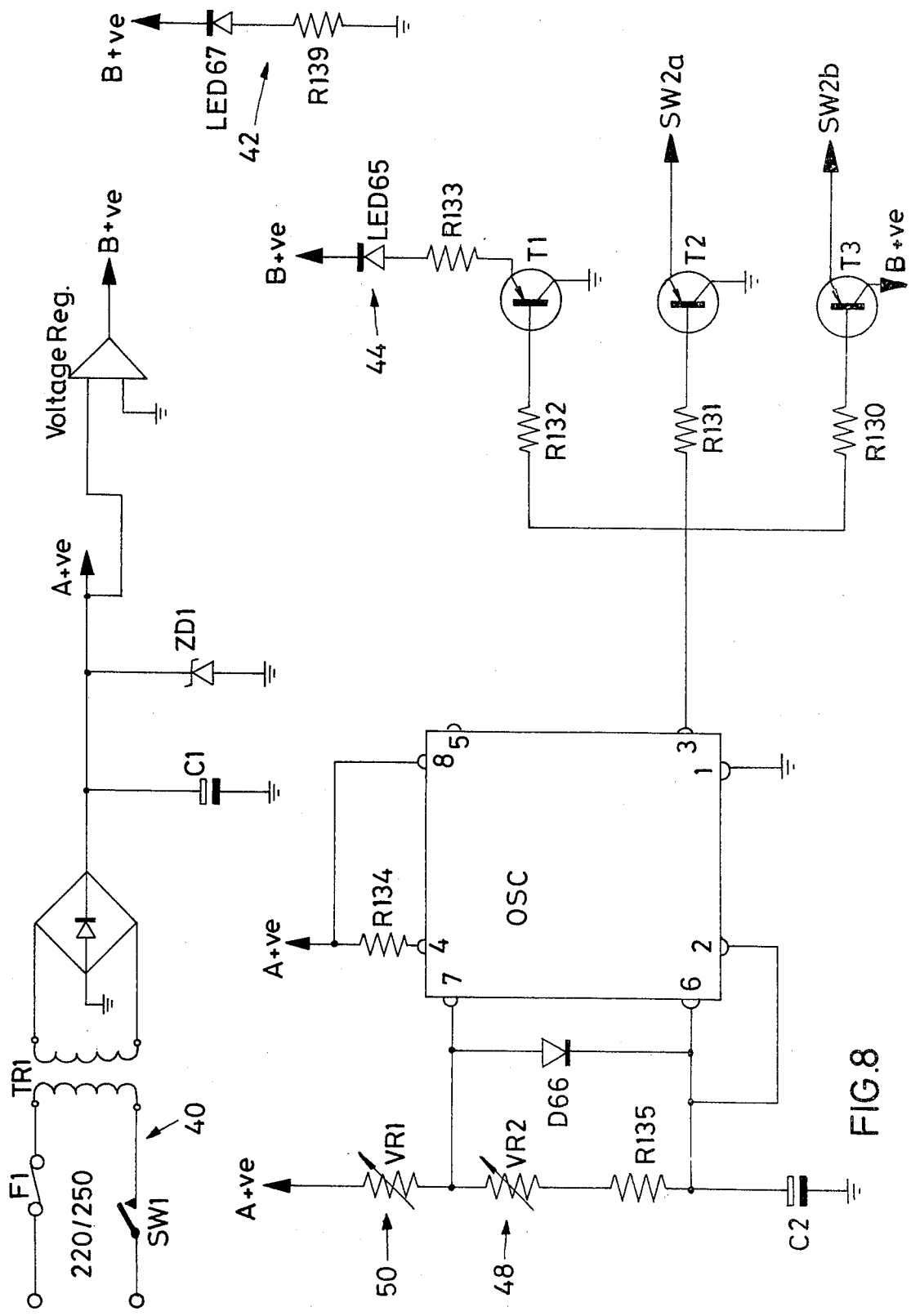
Figure 9:
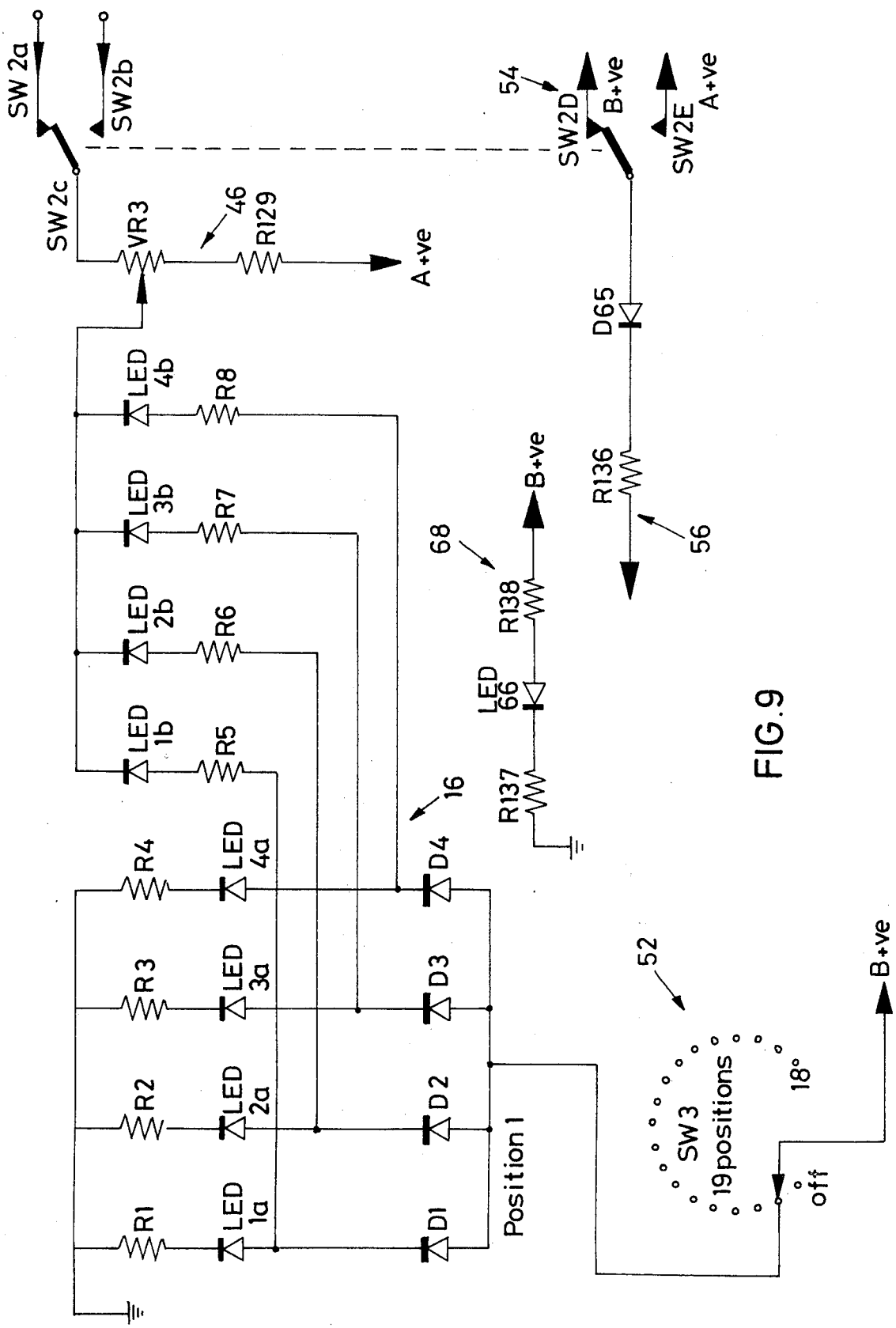

FIG. 1 a pictorial view of the eye testing apparatus in accordance with the invention;

FIG. 2 a side view of the eye testing apparatus assembled together for transportation purposes;

FIG. 3 a front view of the display panel of the control unit of the eye testing apparatus illustrated in FIG. 1, but on a larger scale;

FIG. 4 a side view of the electrical contact provided between the stylus contact and the brass sheath surrounding a light on the display panel illustrated in FIG. 3;

FIG. 5 a side view of the scanner unit of the eye testing apparatus illustrated in FIG. 1;

FIG. 6 a front view of the display panel of the scanner unit as seen along arrows VI—VI in FIG. 5;

FIG. 7 a test sheet to be placed on the control unit of the device illustrated in FIG. 1, but being shown on a slightly larger scale; and FIGS. 8 and 9 a schematic layout of the electronic circuit of the device of FIG. 1.

Referring to FIG. 1, the eye testing apparatus, generally indicated by reference numeral 10, includes a control unit 12 and a scanner unit 14 connected by means of a multi-core electrical cable 16. These units 12 and 14 can be connected together for purposes of transportation as shown in FIG. 2 in that two hook connections 18 join the units 12 and 14 so that the apparatus 10 can be carried by means of the handles 20 provided on the scanner unit 14. The control unit 12 is connected by means of cable 21 (see FIG. 3) to a source of electrical energy, e.g. a mains supply or a battery supply. Alternatively, the control unit 12 may have its own built-in power supply, e.g. in the form of batteries.

Referring now also to FIG. 3, the scanner unit 12 is provided with a housing 22 including all electrical and electronic parts and circuitry, and a display plate 24 on which various parts are displayed as well as having the various control elements. The display plate 24 has a control light display panel 26, which includes a center 28 surrounded by five concentric circles or meridians 30 marked at equal distances in units 5, 10, 15, 20 and 25. Further there are provided radial lines 32 at various angular positions spaced in 15° intervals and indicated from 0° to 180° on the top half and from 0° to 180° on the bottom half. On the display panel 26 a number of electrical light bulbs 34, which protrude for a small distance from the face of the panel 26, are provided. The left eye blind spot is approximately indicated by the lines 36 and that of the right eye by 38. Each light 34 is surrounded by a brass sheath 34.1 for contact purposes (see FIG. 4).

The following control or indicating elements are provided:

40: On-off main switch.
42: On-off indicating light for indicating supply from mains.

44: A control light which will flash on the control unit 12 corresponding to the flash of the lights in the scanner unit 14.

46: A control switch for varying the intensity of light flashes in the scanner unit 14. This variation can be between 0.1 to 1.0 mcd.

48: A control switch for varying the duration of the light flashes in the scanner unit 14. The duration can vary between 0.01 and 0.04 seconds.

50: A control switch for varying the interval between the light flashes in the scanner unit 14. This interval can vary between 1 to 5 seconds.

52: A selector switch which enables a group of the lights 34 on the display panel 26 to be illuminated simultaneously and which will cause the corresponding lights in the scanner unit 14 to flash. As is shown eighteen different groups are provided.

54: A switch for allowing either a group of the lights 34 to be illuminated by operation of the selector switch 52 or, if switched to the right hand side, to allow only a single light to be illuminated by means of the stylus contact 56.

56: An electrical conducting stylus connected by means of an extensible coil cable 58 to the circuitry provided in the control unit 12, which stylus 56, when connected with the metal sheath 34.1 surrounding a light 34, causes such a light to be illuminated as well as the corresponding light in the scanner unit 14.

16: A multi-core cable connecting the lights 34 to the corresponding lights on the display panel in the scanner unit 14.

FIG. 4 shows a side view of the display plate 24 and a light 34 mounted on it. The light 34 is surrounded by a metal sheath 34.1. By touching the stylus 56, as indicated, contact is made and the light 34 is illuminated as well as the corresponding light in the scanner unit 14.

Referring now also to FIGS. 5 and 6, the scanner unit 14 includes a fully enclosed housing comprising a box shaped part 60 and a funnel shaped hood 62 connected to it. In the box shaped part 60 a scanner display panel 64 is provided and on this there are provided lights 66 corresponding in position to the lights 34 on the display panel 26. In the center a fixation light 68 is provided. All the lights 66 and the lights 34 are interconnected by means of the multi-core cable 16 so that corresponding lights are always illuminated simultaneously.

The scanner display panel 64 is curved approximately to correspond to the retina of the eye.

The funnel hood 62 has an opening 70 for an eye piece in which various lenses can be inserted, if required. These lenses may be coloured, e.g. red to detect particular eye diseases or abnormalities, or convex lenses to enlarge the field of vision to be tested.

Two handles 20 are provided on the housing 60 for allowing a patient to hold the scanner unit 14 when looking through the eye-piece 70. These handles 20 also serve for carrying the assembled apparatus as is illustrated in FIG. 2.

In FIG. 7 a typical test sheet 72 is illustrated. This test sheet 72 corresponds with the display panel 26 by having concentric circles or meridians 74 corresponding to the concentric circles or meridians 30 and radial lines 76 corresponding to the radial lines 32. At the position of the lights 34 on the panel 26, holes 78 are provided in the sheet 72 so that this sheet 72 can be fitted exactly in position on the display panel 26 with the lights 34 and sheaths 34.1 protruding through the holes 78. Details regarding the patient to be examined as well as the date and other required details are provided on the sheet 72, and the sheet 72 can be marked by means of the stylus 56 to indicate which lights are not observed by the patient.

For testing the eyes of a patient, the apparatus 10 is provided as shown in FIG. 1. The unit 12 is connected to an electrical power plug by means of the cable 21 and the device is switched on by means of switch 40. The patient holds the scanner unit 14 by means of the handles 20 with one eye occluded and the other eye looking through the eye-piece 70.

With the switch 40 switched on, the central fixation light 68 on the scanner unit 14 will be illuminated. Also the on/off indicating light 42 on the control unit 12 is illuminated.

The operator places a sheet 72 on the panel 24 in position on the display face 26. The operator then moves the control unit 12 slightly behind the patient in order not to disturb him. The operator then adjusts the three control switches marked 46, 48 and 50, which set the flash intensity, the flash duration and the flash interval, according to his professional judgment, taking into account the patient's visual acuity, age and mental reaction time.

When set at upright position, these three controls 46, 48 and 50 are correctly set for an average patient of 50 years of age.

The switch 54 is set to group pattern, i.e. the left hand side.

The operator then directs the patient to look at the centrally fixation light 68. The operator turns switch 52 to position "1" and asks the patient how may lights he sees. The corresponding lights 66 flash in the scanner 14 and corresponding patterns of lights 34 will be illuminated on the control unit 26. The patient will answer how many lights he sees. If the correct number is given, the operator will proceed to the next position of the switch. Thus, if four lights are illuminated on the control unit 12, and the patient replies four, or if three lights are illuminated and the patient replies three, the next position of the switch is activated, causing a different group of lights to be illuminated. The procedure is repeated until all eighteen of the switch positions and eighteen patterns have been flashed. The groups may have a regular pattern for say the first two groups so as to put the patient at ease, whereas later groups are selected to eliminate the chance of anticipation in the patient's mind.

Should however the patient reply three, if four lights are illuminated, the operator will activate switch 54 to the right to the position of single light, which will leave the four lights illuminated on the control unit 12, but will allow no light pattern to flash in the scanner unit 14. He then uses his self-marking stylus 56 and touches each light in turn. As he touches that light, its corresponding light in the scanner unit 14 will flash. If the patient sees this light flashing while looking at the central fixation light 68, he proceeds to the next. One light obviously will not be seen. The operator then rings this light on his paper sheet 72 by means of the stylus 56 as being within a scotoma, and proceeds back to the group pattern system by moving the switch 54 to the left.

At the end of the test, the lights which were not seen as groups and not seen when flashed individually, will have their positions marked on the paper sheet 72, and if these are connected by drawing a rough circle around their perimeter, they represent the outline and position of the scotoma.

The test is repeated with the other eye of the patient.

In addition, in order to test people of low intelligence, the group switch 52 is left on the "off" position. The switch 54 is placed to single light position. The patient holds the scanner unit 14 in the manner as described above. The operator touches the stylus 56 to the sheath 34.1 of each light 34 in turn and the patient, while looking at the central fixation light 68, reports whether or not he can see a light. In this manner, the patient only has to observe one light at a time. Those lights not seen, have their position on the control panel ringed in order to outline the shape of the scotoma.

The control unit 12 consists of four printed circuit boards with the light emitting diodes mounted on one of them.

The light emitting diodes in the control unit 12 are set into metal sheaths 34.1 which protrude through the control plate 24. These metal sheaths 34.1 are common to the light emitting diode anodes. The master switch 52 controlling the patterns, activates the anode of each light emitting diode for that pattern in the control unit 12 and in the scanner unit 14.

The common cathodes of the light emitting diodes in the scanner unit 14 are connected to the zero volt line via an electronic switch which is controlled by an oscillator. The oscillator has three controls, which enable the duration of the flash, the interval between flashes, and the intensity of the light emitting diodes to be controlled, i.e. by means of switches 46, 48, 50.

Activating switch 54 isolates the common cathode line to the scanner unit 14. If the self-inking stylus 56, which is connected to the positive volt line, is applied to the metal sheath 34.1 around the light 34, it will activate its corresponding light emitting diode in the scanner unit 74. If the switch 52 is set to "off", the power via the stylus 56 will activate only the light emitting diode on the control panel 26 and its corresponding light emitting diode in the scanner unit 14.

FIGS. 8 and 9 show a schematic layout of an electronic circuit of the control unit 12. The connection points to the various switches are referred to by the same reference numerals.

I claim:

1. An eye testing apparatus including a control unit having a control display panel having a number of distributed electrical lights adapted to be illuminated; an electrical connection means for connecting the control unit to a source of electrical energy; a remote scanner unit adapted to be electrically connected to the control unit, and including a scanner display panel provided with electrical lights, positioned corresponding to the lights on the control display panel, and which are adapted to be illuminated corresponding to the illumination of the lights on the control display panel, the scanner display panel also having a fixing light; and operation means for causing any one or more lights on the control display panel and the corresponding light or lights on the scanner display panel to be illuminated for observation by a person viewing the scanner display panel.

2. An eye testing apparatus as claimed in claim 1, in which each light is provided with an electrical contact by means of which such light can be caused to be illuminated.

3. An eye testing apparatus as claimed in claim 2, in which the electrical contact is in the form of an electrically conducting sheath surrounding the light.

4. An eye testing apparatus as claimed in claim 1, in which the operation means includes an electrically conducting marking device, connected by means of a cable to the control unit, and on contact with the electrical contact of a light causing such light to be illuminated.

5. An eye testing apparatus as claimed in claim 1, including flashing means for illuminating the lights in flashing manner.

6. An eye testing apparatus as claimed in claim 5, which includes duration adjustment means for varying the period and duration of flash of the lights.

7. An eye testing apparatus as claimed in claim 1, in which the scanning unit includes a housing fully enclosing the scanner display panel, the housing having a viewing opening adapted to be placed for observation against the eye of a person.

8. An eye testing apparatus as claimed in claim 1, in which the scanner unit includes a box shaped housing including the scanner display panel and a funnel shaped hood having a converging part, and a viewing opening being provided in the converging part of the funnel shaped hood.

9. An eye testing apparatus as claimed in claim 1, which includes light intensity adjusting means for varying the light intensity of the lights.

10. An eye testing apparatus as claimed in claim 1, in which group control means is provided for allowing a group of lights to be illuminated simultaneously.

11. An eye testing apparatus as claimed in claim 1, in which the control display panel of the control unit has locating means for locating a test sheet to be placed on the control display panel.

12. As eye testing apparatus as claimed in claim 11, in which the locating means is provided in that the lights on the control display panel stand proud of the display panel for allowing location of a test sheet provided with openings corresponding to the lights.

* * * * *